(12) United States Patent
Klimko

(10) Patent No.: US 6,576,663 B2
(45) Date of Patent: Jun. 10, 2003

(54) 6-KETO PROSTAGLANDIN $F_{1\alpha}$ AND ANALOGS FOR TREATING DRY EYE

(75) Inventor: Peter G. Klimko, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 09/787,788

(22) PCT Filed: Dec. 22, 2000

(86) PCT No.: PCT/US00/35442

§ 371 (c)(1),
(2), (4) Date: Mar. 23, 2001

(87) PCT Pub. No.: WO01/46134

PCT Pub. Date: Jun. 28, 2001

(65) Prior Publication Data

US 2002/0137793 A1 Sep. 26, 2002

Related U.S. Application Data

(60) Provisional application No. 60/171,736, filed on Dec. 22, 1999, now abandoned.

(51) Int. Cl.[7] ............... A61K 31/215; A61K 31/19; C07C 69/76; C07C 59/48; C07C 405/00
(52) U.S. Cl. ............... 514/530; 514/568; 560/60; 562/470; 562/471; 562/503
(58) Field of Search ............... 514/530, 568; 560/60; 562/470, 471, 503

(56) References Cited

U.S. PATENT DOCUMENTS

| | | |
|---|---|---|
| 3,991,759 A | 11/1976 | Urquhart |
| 4,131,651 A | 12/1978 | Shah et al. |
| 4,158,667 A * | 6/1979 | Axen |
| 4,304,783 A * | 12/1981 | Beck et al. |
| 4,370,325 A | 1/1983 | Packman |
| 4,409,205 A | 10/1983 | Shively |
| 4,499,293 A | 2/1985 | Johnson et al. |
| 4,744,980 A | 5/1988 | Holly |
| 4,753,945 A | 6/1988 | Gilbard et al. |
| 4,818,537 A | 4/1989 | Guo |
| 4,868,154 A | 9/1989 | Gilbard et al. |
| 4,883,658 A | 11/1989 | Holly |
| 4,914,088 A | 4/1990 | Glonek et al. |
| 4,966,773 A | 10/1990 | Gressel et al. |
| 5,041,434 A | 8/1991 | Lubkin |
| 5,075,104 A | 12/1991 | Gressel et al. |
| 5,151,444 A | 9/1992 | Ueno et al. |
| 5,290,572 A | 3/1994 | MacKeen |
| 5,294,607 A | 3/1994 | Glonek et al. |
| 5,403,841 A | 4/1995 | Lang et al. |
| 5,455,265 A | 10/1995 | Chandraratna |
| 5,620,921 A | 4/1997 | Sullivan |
| 5,696,166 A | 12/1997 | Yanni et al. |

FOREIGN PATENT DOCUMENTS

| | | |
|---|---|---|
| DE | 2840032 | 3/1979 |
| EP | 0009869 A2 | 4/1980 |
| EP | 0019069 A2 | 11/1980 |
| EP | 0156611 A2 | 10/1985 |
| EP | 0289349 A1 | 11/1988 |
| EP | 0308135 A2 | 3/1989 |
| EP | 0561073 A1 | 9/1993 |
| WO | 00/38663 | 7/2000 |

OTHER PUBLICATIONS

Kulkarni et al Prostaglandins, Jun. 1986, 13(6), pp. 1159–1164.*

Benedetto, C., R.G. McDonald–Gibson, S. Nigam, and T.F. Slater, Eds., *Prostaglandins and Related Substances: A Practical Approach*; IRL Press: Oxford, pp. 13–16 (1987).

Blume et al., *Activated Endothelial Cells Elicit Paracrine Induction of Epithelial*, J. Clin. Invest., 102:1161 (1998).

Coleman et al., *VIII International Union of Pharmacology classification of prostanoid receptors: Properties, distribution, and structure of the receptors and their subtypes*, Pharmacological Reviews, 45:205–229 (1994).

Dartt et al., *Vasoactive intestinal peptide–stimulated glycoconjugate secretion from conjunctival goblet cells*, Experimental Eye Research, 63:27–34 (1996).

Dilly et al., *Surface Changes in the Anaesthetic Conjunctiva in Man, with Special Reference to the Production of Mucus from a Non–Goblet–Cell Source*, British Journal of Ophthalmology, 65:833–842 (1981).

Gilbard, *Dry eye: pharmacological approaches, effects, and progress*, The CLAO Journal, 22:141–145 (1996).

Gipson and Inatomi, *Mucin genes expressed by ocular surface epithelium*, Progress in Retinal and Eye Research, 16:81–98 (1997).

Greiner et al., *Mucus Secretory Vesicles in Conjunctival Epithelial Cells of Wearers of Contact Lenses*, Archives of Ophthalmology, 98:1843–1846 (1980).

Lemp, *Report of the Nation Eye Institute/Industry Workshop on Clinical Trials in Dry Eyes*, The CLAO Journal, 21(4):221–231 (1995).

Nakamura et al., *Gefarnate stimulates secretion of mucin–like glycoproteins by corneal epithelium in vitro and protects corneal epithelium from dessication in vivo*, Experimental Eye Research, 65:569–574 (1997).

Schein et al., *Prevalence of dry eye among the elderly*, American J. Ophthalmology, 124:723–738 (1997).

Watanabe et al., *Human Corneal and Conjuctival Epithelia Produce a Mucin–Like Glycoprotein for the Apical Surface*, Investigative Ophthalmology and Visual Science (IOVS), 36(2):337–344 (1995).

Yanni et al., *Effect of Intravenously Administered Lipoxygenase Metabolites on Rat Trachael Mucous Gel Layer Thickness*, International Archives of Allergy And Applied Immunology, 90:307–309 (1989).

* cited by examiner

Primary Examiner—Samuel Barts
Assistant Examiner—Paul A. Zucker
(74) Attorney, Agent, or Firm—Barry L. Copeland

(57) ABSTRACT

Compositions and methods for the treatment of dry eye and related diseases utilizing 6-keto-$PGF_{1\alpha}$ and its analogs are disclosed.

7 Claims, No Drawings

6-KETO PROSTAGLANDIN $F_{1\alpha}$ AND ANALOGS FOR TREATING DRY EYE

RELATED APPLICATIONS

This is a national application under 35 U.S.C. §371 of PCT/US0035442 filed Dec. 22, 2000, which draws priority from U.S. Provisional Application Serial No. 60/171,736 filed Dec. 22, 1999, now abandoned.

FIELD OF THE INVENTION

The present invention relates to the use of 6-keto $PGF_{1\alpha}$ and analogs thereof to stimulate mucin secretion to treat dry eye, keratoconjunctivitis, Sjogren's syndrome and related ocular surface diseases.

BACKGROUND OF THE INVENTION

Dry eye is a common ocular surface disease afflicting millions of people in the U.S. each year, especially the elderly (Schein et. al., *Prevalence of dry eye among the elderly. American J. Ophthalmology,* 124:723–738, (1997)). Dry eye may afflict an individual with varying severity. In mild cases, a patient may experience burning, a feeling of dryness, and persistent irritation such as is often caused by small bodies lodging between the eye lid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, the common end result is the breakdown of the tear film, which results in dehydration of the exposed outer surface of the eye. (Lemp, *Report of the Nation Eye Institute/Industry Workshop on Clinical Trials in Dry Eyes, The CLAO Journal,* 21(4):221–231 (1995)). Four events have been identified which singly or in combination are believed to result in the dry eye condition: a) decreased tear production or increased tear evaporation; b) decreased conjunctival goblet-cell density; c) increased corneal desquamation; and d) destabilization of the cornea-tear interface (Gilbard, *Dry eye: pharmacological approaches, effects, and progress. The CLAO Journal,* 22:141–145 (1996)). Another major problem is the decreased mucin production by the conjunctival cells and/or corneal epithelial cells of mucin, which protects and lubricates the ocular surface (Gipson and Inatomi, *Mucin genes expressed by ocular surface epithelium. Progress in Retinal and Eye Research,* 16:81–98 (1997)).

Practitioners have taken several approaches to the treatment of dry eye. One common approach has been to supplement and stabilize the ocular tear film using so-called artificial tears instilled throughout the day. Another approach has been the use of ocular inserts that provide a tear substitute or to stimulate endogenous tear production.

Examples of the tear substitution approach include the use of buffered, isotonic saline solutions, aqueous solutions containing water soluble polymers that render the solutions more viscous and thus less easily shed by the eye. Tear reconstitution is also attempted by providing one or more components of the tear film such as phospholipids and oils. Examples of these treatment approaches are disclosed in U.S. Pat. Nos. 4,131,651 (Shah et. al.), 4,370,325 (Packman), 4,409,205 (Shively), 4,744,980 and 4,883,658 (Holly), 4,914,088 (Glonek), 5,075,104 (Gressel et. al.) and 5,294,607 (Glonek et. al.).

United States Patents directed to the use of ocular inserts in the treatment of dry eye include U.S. Pat. No. 3,991,759 (Urquhart). Other semi-solid therapy has included the administration of carrageenans (U.S. Pat. No. 5,403,841, Lang) which gel upon contact with naturally occurring tear film.

Another recent approach involves the provision of lubricating substances in lieu of artificial tears. U.S. Pat. No. 4,818,537 (Guo) discloses the use of a lubricating, liposome-based composition.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye condition in post-menopausal women; U.S. Pat. No. 5,290,572 (MacKeen) discloses the use of finely divided calcium ion compositions to stimulate tear film; and U.S. Pat. No. 4,966,773 (Gressel et. al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective treatment for dry eye that is capable of alleviating symptoms, as well as treating the underlying physical and physiological deficiencies of dry eye, and that is both convenient and inexpensive to administer.

Mucins are proteins which are heavily glycosylated with glucosarnine-based moieties. Mucins provide protective and lubricating effects to epithelial cells, especially those of mucosal membranes. Mucins have been shown to be secreted by vesicles and discharged on the surface of the conjuctival epithelium of human eyes (Greiner et. al., *Mucus Secretory Vesicles in Conjunctival Epithelial Cells of Wearers of Contact Lenses, Archives of Ophthalmology,* 98:1843–1846 (1980); and Dilly et. al., *Surface Changes in the Anaesthetic Conjunctiva in Man, with Special Reference to the Production of Mucus from a Non-Goblet-Cell Source, British Journal of Ophthalmology,* 65:833–842 (1981)). A number of human-derived mucins which reside in the apical and subapical corneal epithelium have been discovered and cloned (Watanabe et. al., *Human Corneal and Conjuctival Epithelia Produce a Mucin-Like Glycoprotein for the Apical Surface, Investigative Ophthalmology and Visual Science (IOVS),* 36(2):337–344 (1995)). Recently, a new mucin was reported to be secreted via the cornea apical and subapical cells as well as the conjunctival epithelium of the human eye (Watanabe et. al., *IOVS,* 36(2):337–344 (1995)). These mucins provide lubrication, and additionally attract and hold moisture and sebacious material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et. al., *Effect of Intravenously Administered Lipoxygenase Metabolites on Rat Trachael Mucous Gel Layer Thickness, International Archives of Allergy And Applied Immunology*, 90:307–309 (1989)).

The conventional treatment for dry eye, as discussed above, includes administration of artificial tears to the eye several times a day. Other agents claimed for increasing ocular mucin and/or tear production include vasoactive intestinal polypeptide (Dartt et. al., *Vasoactive intestinal peptide-stimulated glycocongfugate secretion from conjunctival goblet cells. Experimental Eye Research*, 63:27–34, (1996)), gefarnate (Nakmura et. al., *Gefarnate stimulates secretion of mucin-like glycoproteins by corneal epithelium in vitro and protects corneal epithelium from dessication in vivo, Experimental Eye Research*, 65:569–574 (1997)), and the use of liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), retinoids (U.S. Pat. No. 5,455,265) and hydroxyeicosatetraenoic acid derivatives (U.S. Pat. No. 5,696,166). However, many of these compounds or treatments suffer from a lack of specificity, efficacy and potency and none of these agents have been marketed so far as therapeutically useful products to treat dry eye and related ocular surface diseases. Thus, there remains a need for an efficacious therapy for the treatment of dry eye and related diseases.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins are known in the art including A, B, C, D, E, F, G, I and J-Series prostaglandins (U.S. Pat. No. 5,151,444; EP 0 561 073 A1; Coleman et. al., *VIII International Union of Pharmacology classification of prostanoid receptors: Properties, distribution, and structure of the receptors and their subtypes, Pharmacological Reviews*, 45:205–229 (1994)). Depending on the number of double-bonds in the α-(top chain) and/or the ω-chain (bottom chain), the prostaglandins are further classified with subscripts such as $PGD_2$, $PGE_1$, $PGE_2$, $PGF_{2\alpha}$, etc. (U.S. Pat. No. 5,151,444; Coleman et. al., *VIII International Union of Pharmacology classification of prostanoid receptors: Properties, distribution, and structure of the receptors and their subtypes, Pharmacological Reviews*, 45:205–229 (1994)). Whilst these classes of prostaglandins interact preferably with the designated major classes of receptors (e.g. DP, EP, FP) and subclasses of receptors (e.g. $EP_2$, $EP_3$, $EP_4$), the subscripts associated with the prostaglandin does not necessarily correspond with the subclass of the receptor(s) with which they interact. Furthermore, it is well known that these endogenous prostaglandins are non-specific in terms of interacting with the various classes of prostaglandin receptors. Thus, the natural prostaglandin $PGE_2$ not only interacts with $EP_2$ receptors, but can also activate $EP_1$, $EP_3$ and $EP_4$ receptors (Coleman et. al., *VIII International Union of Pharmacology classification of prostanoid receptors: Properties, distribution, and structure of the receptors and their subtypes, Pharmacological Reviews*, 45:205–229 (1994)).

The compound 6-keto-$PGF_{1\alpha}$(1) is a known stable hydrolysis product of $PGI_2$ in mammals, and is frequently used as a marker for the determination of $PGI_2$ in blood and urine (*Prostaglandins and Related Substances: A Practical Approach;* C. Benedetto, R. G. McDonald-Gibson, S. Nigam, and T. F. Slater, Eds.; IRL Press: Oxford, 1987, pp. 13–16). Recently, it has been found that 6-keto $PGF_{1\alpha}$ is a potent chloride secretagogue released by intestinal epithelial cells in response to hypoxia [Colgan et. al., *J. Clin. Invest.*, 102:1161(1998)]. Of interest in the present invention are 1 and its structural analogs.

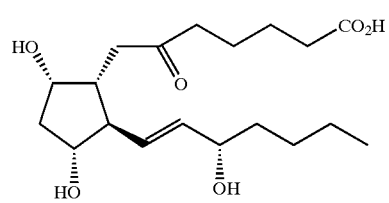

SUMMARY OF THE INVENTION

The present invention is directed to compositions and methods for the treatment of dry eye and other disorders requiring the wetting of the eye. More specifically, the present invention discloses compositions containing 6-keto $PGF_{1\alpha}$ and its analogs, and methods of their use for treating dry eye type disorders.

Preferred compositions include an effective amount of 6-keto $PGF_{1\alpha}$ or an analog thereof for the production of mucins. The compositions are administered topically to the eye for the treatment of dry eye.

DETAILED DESCRIPTION OF THE INVENTION

It has now been discovered that 6-keto $PGF_{1\alpha}$ and its analogs stimulate mucin production in human conjuctival epithelium and are therefore believed to be useful in treating dry eye. Specifically included are compounds of the following formula I:

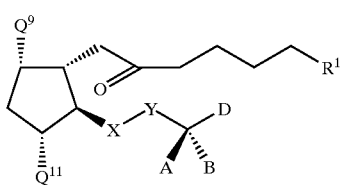

wherein:
$R^1$ is $(CH_2)_pCO_2R$, $(CH_2)_pOR^2$, $(CH_2)_pCOT$, or $(CH_2)_pT$, where:
  R is H or pharmaceutically acceptable cationic salt moiety, or $CO_2R$ forms a pharmaceutically acceptable ester moiety;
  $OR^2$ forms a free or functionally modified hydroxy group, where $R^2$ is preferably H, alkyl, acyl, or aryl;
  T comprises a free or functionally modified amino group and is preferably $NR^3R^4$
    where $R^3$ and $R^4$, are the same or different and are selected from the group consisting of H, alkyl, aryl, acyl, alkoxycarbonyl, alkoxy, aminocarbonyl, and hydroxy; and
  p is 0 or 2;
$Q^9$ and $Q^{11}$ form a free or functionally modified hydroxy group and are preferably $R^9O$ and $R^{11}O$, respectively, where $R^9$ and $R^{11}$ are the same or different and are preferably H, alkyl, acyl, or aryl;

X—Y is $CH_2CH_2$, trans-CH=CH, or C≡C;

one of A, B is H and the other comprises a free or functionally modified hydroxy group, or A-B together are the oxygen of a carbonyl group; and D is cycloalkyl, $C_{5-8}$ alkyl, $(CH_2)_q Ar$ or $(CH_2)_q OAr$; where q is 1–6; and Ar is a phenyl ring optionally substituted with alkyl, halo, trihalomethyl, alkoxy, acyl, acyloxy, amino, alkylamino, acylamino, or hydroxy; or D is $(CH_2)_p Ar^1$; where p is 0–6; and

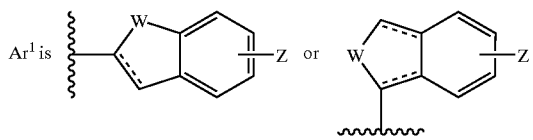

wherein:

W is $CH_2$, O, $S(O)_m$, $NR^{10}$, $CH_2CH_2$, CH—CH, $CH_2O$, $CH_2S(O)_m$, CH—N, or $CH_2NR^{10}$; where m is 0–2, and $R^{10}$ is H, alkyl, or acyl; Z is H, alkyl, alkoxy, acyl, acyloxy, halo, trihalomethyl, amino, alkylamino, acylamino, or hydroxy; and

- - - - - is single or double bond.

It is believed that the compounds of formula I wherein D is selected from the group consisting of $(CH_2)_q Ar$, $(CH_2)_q OAr$, $(CH_2)_p Ar^1$, and cycloalkyl, where p, q, Ar, and $Ar^1$ are as defined above, are novel.

It is appreciated that those compounds of formula I wherein $R^9$ is H (i.e., where a hydroxyl group is present at carbon 9) exist as an equilibrium mixture of ketoalcohol i and hemiketal ii isomers, with the latter usually being the predominant or even exclusive isomer. Both forms are included within the scope of the invention. For convenience, only the ketoalcohol form is depicted in the specification and claims.

volumes 1–5; *Principles of Asymmetric Synthesis;* R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (A *Practical Guide to Chiral Separations by HPLC;* G. Subramanian, Ed.; VCH Publishers: New York, 1994; *Chiral Separations* by HPLC; A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions,* volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

As used herein, the terms "pharmaceutically acceptable salt" and "pharmaceutically acceptable ester/pharmaceutically acceptable thioester" means any salt, ester, or thioester, respectively, that would be suitable for therapeutic administration to a patient by any conventional means without significant deleterious health consequences; and "ophthalmically acceptable salt", "ophthalmically acceptable ester", and "ophthalmically acceptable thioester" means any pharmaceutically acceptable salt, ester, or thioester, respectively, that would be suitable for ophthalmic application, i.e. non-toxic and non-irritating.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxy-

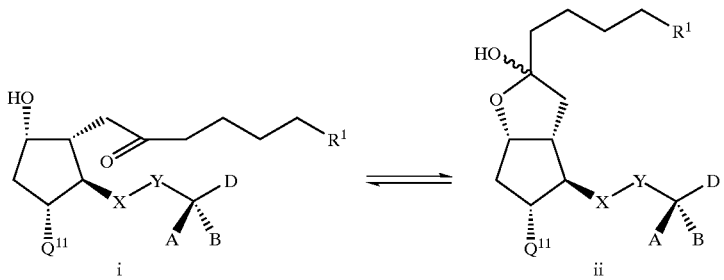

Included within the scope of the present invention are the individual enantiomers of the compounds of the present invention, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (Asymmetric Synthesis; J. D. Morrison and J. W. Scott, Eds.; Academic Press Publishers: New York, 1983–1985, carbonyl group is substituted for the hydrogen. Preferred moieties include OH, $OCH_2C(O)CH_3$, $OCH_2C(O)C_2H_5$, $OCH_3$, $OCH_2CH_3$, $OC(O)CH_3$, and $OC(O)C_2H_5$.

The term "free amino group" means an $NH_2$. The term "functionally modified amino group" means an $NH_2$ which has been functionalized to form: an aryloxy-, heteroaryloxy-, alkoxy-, cycloalkoxy-, heterocycloalkoxy-, alkenyl-, cycloalkenyl-, heterocycloalkenyl-, alkynyl-, or hydroxy-amino group, wherein the appropriate group is substituted for one of the hydrogens; an aryl-, heteroaryl-, alkyl-, cycloalkyl-, heterocycloalkyl-, alkenyl-, cycloalkenyl-, heterocycloalkenyl-, or alkynyl-amino group, wherein the appropriate group is substituted for one or both of the hydrogens; an amide, in which an acyl group is substituted for one of the hydrogens; a carbamate, in which an aryloxy-, heteroaryloxy-, alkoxy-, cycloalkoxy-, heterocycloalkoxy-, alkenyl-, cycloalkenyl-, heterocycloalkenyl-, or alkynyl-carbonyl group is substituted for one of the hydrogens; or a urea, in which an aminocarbonyl group is substituted for one of the hydrogens. Combinations of these substitution patterns, for example an $NH_2$ in which one of the hydrogens is replaced by an alkyl group and the other hydrogen is replaced by an alkoxycarbonyl group, also fall under the definition of a functionally modified amino group and are included within the scope of the present invention. Preferred moieties include $NH_2$, $NHCH_3$, $NHC_2H_5$, $N(CH_3)_2$, $NHC(O)CH_3$, NHOH, and $NH(OCH_3)$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or lower alkyl. Preferred cycloalkyl groups include cyclopropyl, cyclobutyl, cyclopentyl and cyclohexyl.

The term "heterocycloalkyl" refers to cycloalkyl rings that contain at least one heteroatom such as O, S, or N in the ring, and can be fused or isolated. The rings may be substituted with other groups, such as halogen, hydroxyl, aryl, aryloxy, alkoxy, or lower alkyl. Preferred heterocycloalkyl groups include pyrrolidinyl, tetrahydrofuranyl, piperazinyl, and tetrahydropyranyl.

The term "alkenyl" includes straight or branched chain hydrocarbon groups having 1 to 15 carbon atoms with at least one carbon—carbon double bond, the chain being optionally interrupted by one or more heteroatoms. The chain hydrogens may be substituted with other groups, such as halogen. Preferred straight or branched alkeny groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon—carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "heterocycloalkenyl" refers to cycloalkenyl rings which contain one or more heteroatoms such as O, N, or S in the ring, and can be fused or isolated. The rings may be substituted with other groups, such as halogen, hydroxyl, aryl, aryloxy, alkoxy, or lower alkyl. Preferred heterocycloalkenyl groups include pyrrolidinyl, dihydropyranyl, and dihydrofuranyl.

The term "carbonyl group" represents a carbon atom double bonded to an oxygen atom, wherein the carbon atom has two free valencies.

The term "aminocarbonyl" represents a free or functionally modified amino group bonded from its nitrogen atom to the carbon atom of a carbonyl group, the carbonyl group itself being bonded to another atom through its carbon atom.

The term "lower alkyl" represents alkyl groups containing one to six carbons ($C_1$–$C_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, halogen, free or functionalized hydroxy, trihalomethyl, etc. Preferred aryl groups include phenyl, 3-(trifluoromethyl)phenyl, 3-chlorophenyl, and 4-fluorophenyl.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group attached through an oxygen linkage.

The terms "alkoxycarbonyl", "aryloxycarbonyl", "heteroaryloxycarbonyl", "cycloalkoxycarbonyl", "heterocycloalkoxycarbonyl", "alkenyloxycarbonyl", "cycloalkenyloxycarbonyl", "heterocycloalkenyloxycarbonyl", and "alkynyloxycarbonyl" represent an alkoxy, aryloxy, heteroaryloxy, cycloalkoxy, heterocycloalkoxy, alkenyloxy, cycloalkenyloxy, heterocycloalkenyloxy, or alkynyloxy group bonded from its oxygen atom to the carbon of a carbonyl group, the carbonyl group itself being bonded to another atom through its carbon atom.

Preferred for purposes of the present invention are those compounds of formula I wherein:

$R^1$ is $CO_2R$, wherein R is H, or $CO_2R$ forms an ophthalmically acceptable salt or an ophthalmically acceptable ester moiety;

$R^9$ and $R^{11}$ are H;

X—Y is $CH_2CH_2$, trans-CH=CH, or C≡C;

one of A, B=H, and the other is OH; and

D is n-$C_5H_{11}$, $CH_2CH_2Ar$, $CH_2OAr$, or cyclohexyl, where Ar is a phenyl ring optionally substituted with halo or trihalomethyl.

Preferred novel compounds are those of formula I wherein:

$R^1$ is $CO_2R$, wherein R is H, or $CO_2R$ forms an ophthalmically acceptable salt or an ophthalmically acceptable ester moiety;

$R^9$ and $R^{11}$ are H;

X—Y is $CH_2CH_2$, trans-CH=CH, or C≡C;

one of A, B=H, and the other is OH; and

D is $CH_2CH_2Ar$, $CH_2OAr$, or cyclohexyl, where Ar is a phenyl ring optionally substituted with halo or trihalomethyl.

Among the most preferred of the foregoing compounds are the following compounds 1–6:

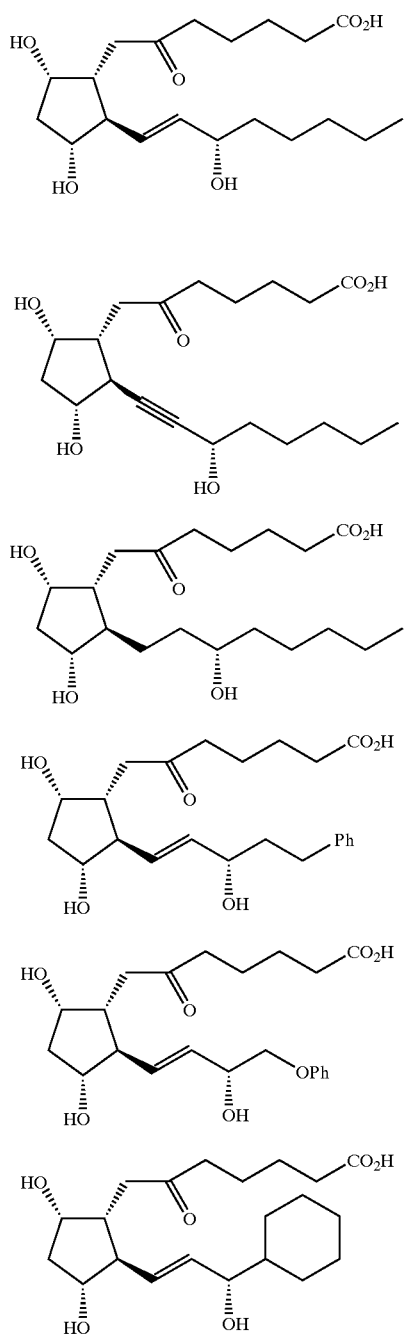

Compound 1 is commercially available from Cayman Chemical Co., Ann Arbor, Mich. The syntheses of compounds 2 and 3 are disclosed in U.S. Pat. Nos. 4,205,178 and 4,158,667. Compounds 4–6 can be prepared as detailed in examples 1–3 (below).

EXAMPLE 1

Synthesis of Compound 4

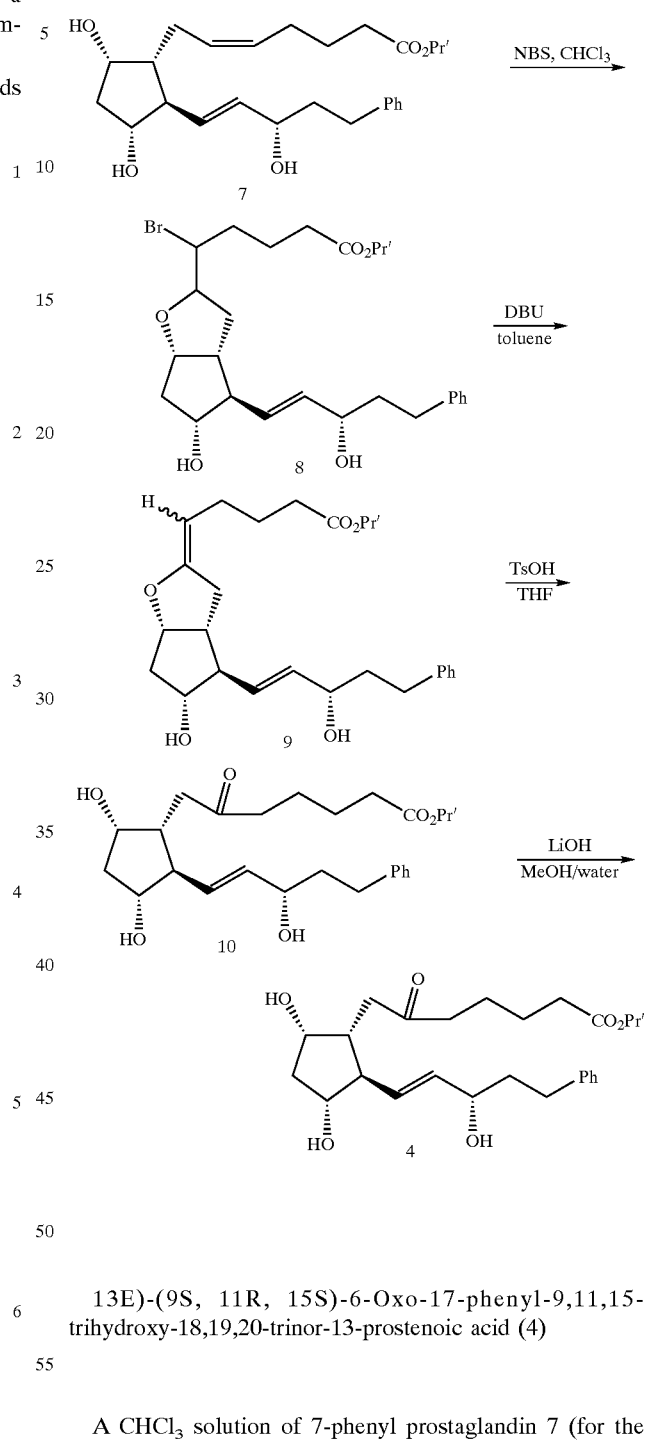

13E)-(9S, 11R, 15S)-6-Oxo-17-phenyl-9,11,15-trihydroxy-18,19,20-trinor-13-prostenoic acid (4)

A $CHCl_3$ solution of 7-phenyl prostaglandin 7 (for the synthesis of 7 see Resul et. al., *J. Med. Chem* 36:2, 243 (1993), as described in Example 1a, is treated with N-br mosuccinimide (NBS) to afford bromoether 8, which is reacted with 1,8-diazabicyclo[5.4.0]-undec-7-ene (DBU) in hot toluene to provide enol ether 9. Heating a THF/water solution of 9 and p-toluenesulfonic acid monohydrate (TsOH) ifords triol 10, which is saponified with LiOH in water/MeOH to give acid 4

EXAMPLE 1a

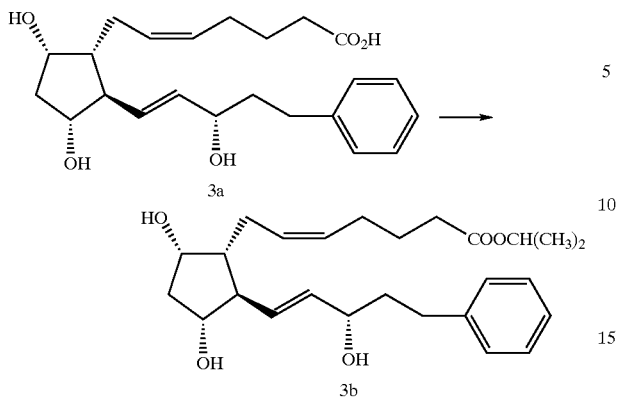

17-Phenyl-18,19,20-trinor-PGF$_{2\alpha}$ Isopropyl Ester (3b). DBU (0.37 g, 2.43 mmol) was added dropwise to a stirred solution of 3a (0.40 g, 0.81 mol) in acetone (16 mL) at 0° C. The mixture was allowed to arm to room temperature whereupon isopropyl iodide 0.41 g, 2.43 mmol) was added dropwise. After being stirred for 10 h (TLC monitoring), the reaction was quenched with water, the mixture was extracted with EtOAc (50 mL), and the extract was washed with brine (20 mL), citric acid 3% (30 mL) and finally sodium hydrogen carbonate 5% (2×20 mL). After drying with anhydrous sodium sulfate, the solvent was removed in vacuo and the residual oil was chromatographe on silica gel using EtOAc as eluent. This afforded 0.34 g (80%) of the title compound as a colorless oil: R$_f$=0.24 (EtOA); [α]$^{20}_D$=+33.49° (c=0.74, CH$_3$CN); $^1$H NMR CDCl$_3$) δ 1.2 (δ, 6 H (CH$_3$)$_2$), 1.46 (m, 1 H), 1.64 (m, 2H), 1.74–1.78 (dd, 1 H), 1.85 (m, 2H), 1.78–1.9 (m, 2 H), 2.08 (m, 2H), 2.23 (t, 2 H, 2.24 (m, 2 H), 2.27 (m, H), 2.3 (m, 1 H), 2.62–2.72 (m, 2), 3.9 (m, 1 H), 4.07 (t, 1 H), 4.13 (m, 1 H), 4.9 (m, 1 H), 5.43–5.59 (m, 4 H), 7.1–7.3 (m, 5 H); $^{13}$C NMR (CDCl$_3$) δ 173.3, 141.9, 128.3, 125.7, 134.6 (C db), 132.03 (C db), 129.6 (C db), 129.04 (C db), 78.01, 72.83, 71.50, 67.5 55.6, 42.9, 38.70, 33.90, 31.70, 26.50, 25.50, 24.80, 21.76, 21.75.

EXAMPLE 2

Synthesis of Compound 5

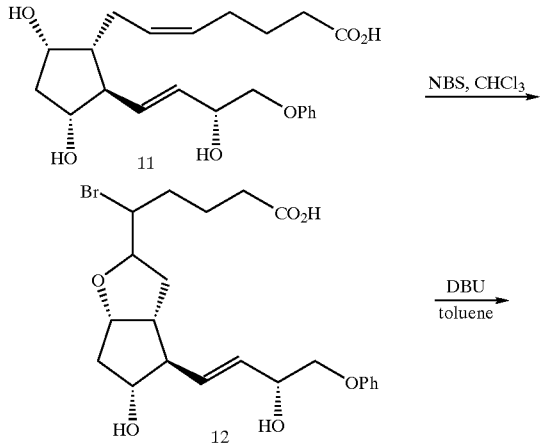

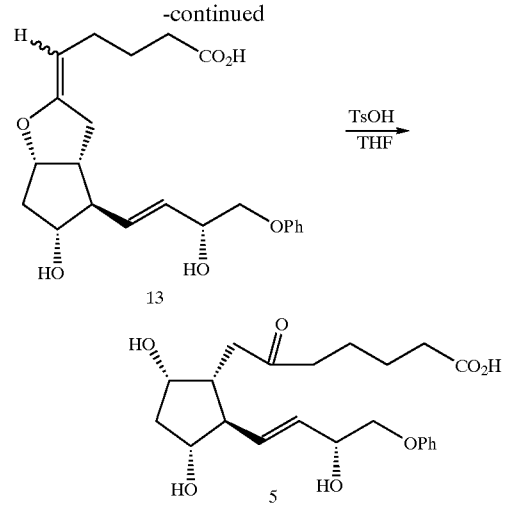

(13E)-(9S, 11R, 15R)-6-Oxo-16-phenoxy-9,11,15-trihydroxy-17,18,19,20-tetranor-13-prostenoic acid (5)

A CHCl$_3$ solution of 16-phenoxy prostaglandin 11 (commercially available from Cayman Chemical Co.) is treated with NBS to afford bromoether 12, which is heated with DBU in toluene to give enol ether 13. Acidic hydrolysis of 13 with TsOH in hot THF/water provides 5.

EXAMPLE 3

Synthesis of Compound 6

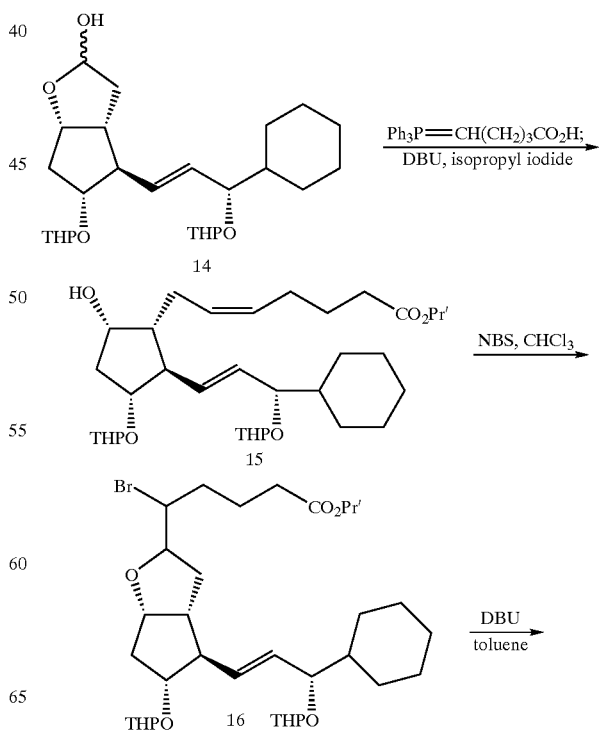

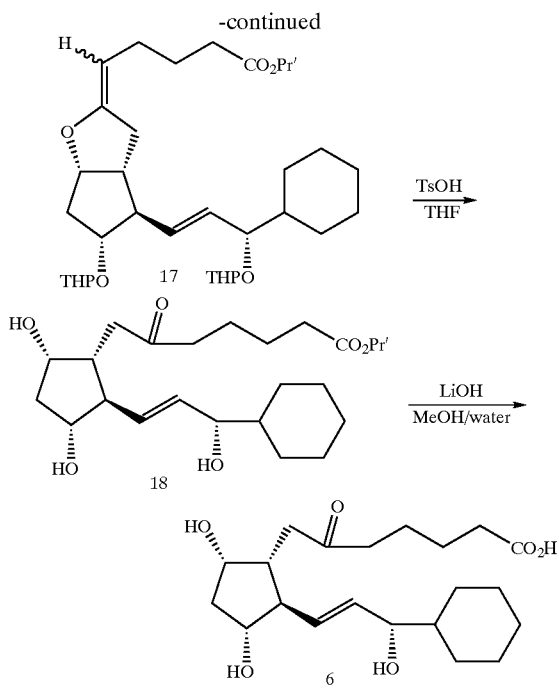

(13E)-(9S,11R,15S)-15-Cyclohexyl-6-oxo-9,11,15-trihydroxy-16,17,18,19,20-pentanor-13-prostenoic acid (6)

Treatment of a THF solution of $Ph_3P^+(CH_2)_4CO_2H\ Br^-$ in at 0° C. with KOBu followed by addition of a THF solution of lactol 14 (for the synthesis of 14, see U.S. Pat. No. 5,807,892, the contents of which are incorporated herein) affords an intermediate diene acid, which is treated with 1,8-diazabicyclo[5.4.0]-undec-7-ene (DBU) and isopropyl iodide in acetone to afford diene 15. A $CHCl_3$ solution of 15 is treated with NBS in THF to provide bromoether 16, which is reacted with DBU in hot toluene to give enol ether 17. Acid hydrolysis of 17 using p-toluenesulfonic acid monohydrate in hot THF/water yields ketotriol 18, which is saponified with LiOH in MeOH/water to afford 6.

The 6-keto $PGF_{1\alpha}$ analogs of the present invention may be contained in various types of pharmaceutical compositions, in accordance with formulation techniques known to those skilled in the art. In general, these compounds will be formulated in solutions for topical ophthalmic administration. Solutions, suspensions and other dosage forms are particularly preferred for the treatment of dry eye.

The ophthalmic compositions of the present invention will include one or more compounds of the present invention in a pharmaceutically acceptable vehicle. Various types of vehicles may be used. Aqueous solutions are generally preferred, based on ease of formulation, biological compatibility, as well as a patient's ability to easily administer such compositions by means of instilling one to two drops of the solutions in the affected eyes. However, the compounds of the present invention may also be readily incorporated into other types of compositions, such as suspensions, viscous or semi-viscous gels, or other types of solid or semi-solid compositions. Suspensions may be preferred for those compounds of the present invention which are less soluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Antioxidants may be added to compositions of the present invention to protect the active ingredient from oxidation during storage. Examples of such antioxidants include vitamin E and analogs thereof, ascorbic acid and butylated hydroxytoluene (BHT).

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

In general, the doses used for the above described purposes will vary, but will be in an effective amount to increase mucin production in the eye and thus eliminate or improve dry eye conditions. As used herein, the term "pharmaceutically effective amount" refers to an amount which improves the dry eye condition in a human patient. When the compositions are dosed topically, they will generally be in a concentration range of from 0.001 to about 1.0% w/v, with 1–2 drops administered 1–4 times per day.

As used herein, the term "pharmaceutically acceptable carrier" refers to any vehicle which, when formulated, is safe, and provides the appropriate delivery for the desired route of administration of an effective amount of at least one compound of the present invention.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method for the treatment of dry eye which comprises administering to a mammal a composition comprising a pharmaceutically acceptable carrier and a pharmaceutically effective amount of one or more compounds of the following formula I:

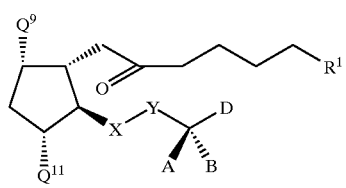

wherein:
R$^1$ is $(CH_2)_pCO_2R$, $(CH_2)_pOR^2$, $(CH_2)_pCOT$, or $(CH_2)_pT$, where:
R is H or pharmaceutically acceptable cationic salt moiety, or $CO_2R$ forms a pharmaceutically acceptable ester moiety;
OR$^2$ forms a free or functionally modified hydroxy group;
T comprises a free or functionally modified amino group; and
p is 0 or 2;

$Q^9$ and $Q^{11}$ form a free or functionally modified hydroxy group;

X—Y is $CH_2CH_2$, trans-CH=CH, or C≡C;

one of A, B is H and the other comprises a free or functionally modified hydroxy group, or A-B together are the oxygen of a carbonyl group; and D is cycloalkyl, $C_{5-8}$ alkyl, $(CH_2)_qAr$ or $(CH_2)_qOAr$; where q is 1–6; and Ar is a phenyl ring optionally substituted with alkyl, halo, trihalomethyl, alkoxy, acyl, acyloxy, amino, alkylamino, acylamino, or hydroxy; or D is $(CH_2)_pAr^1$; where p is 0–6; and $Ar^1$ is

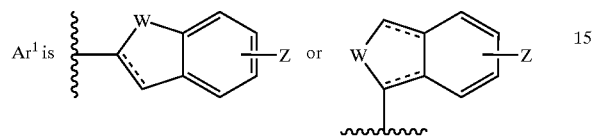

wherein:

W is $CH_2$, O, $S(O)_m$, $NR^{10}$, $CH_2CH_2$, CH=CH, $CH_2O$, $CH_2S(O)_m$, CH=N, or $CH_2NR^{10}$; where m is 0–2, and $R^{10}$ is H, alkyl, or acyl;

Z is H, alkyl, alkoxy, acyl, acyloxy, halo, trihalomethyl, amino, alkylamino, acylamino, or hydroxy; and

----- is single or double bond.

2. The method of claim 1, wherein the mammal is a human and the composition is administered topically.

3. The method of claim 2, wherein for the one or more compounds of formula I:

$R^1$ is $CO_2R$, wherein R is H, or $CO_2R$ forms an ophthalmically acceptable salt or an ophthalmically acceptable ester moiety;

$Q^9$ and $Q^{11}$ are OH;

X—Y is $CH_2CH_2$, trans-CH=CH, or C≡C;

one of A, B=H, and the other is OH; and

D is n-$C_5H_{11}$, $CH_2CH_2Ar$, $CH_2OAr$, or cyclohexyl, where Ar is a phenyl ring optionally substituted with halo or trihalomethyl.

4. The method of claim 3, wherein the one or more compounds of formula I are selected from the group consisting of:

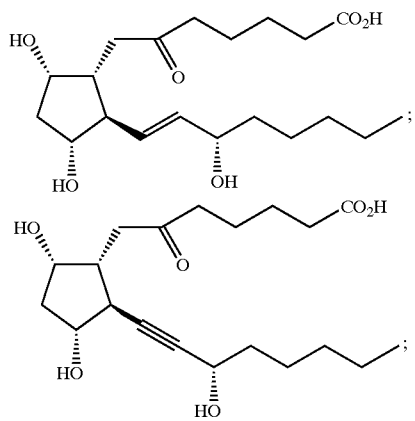

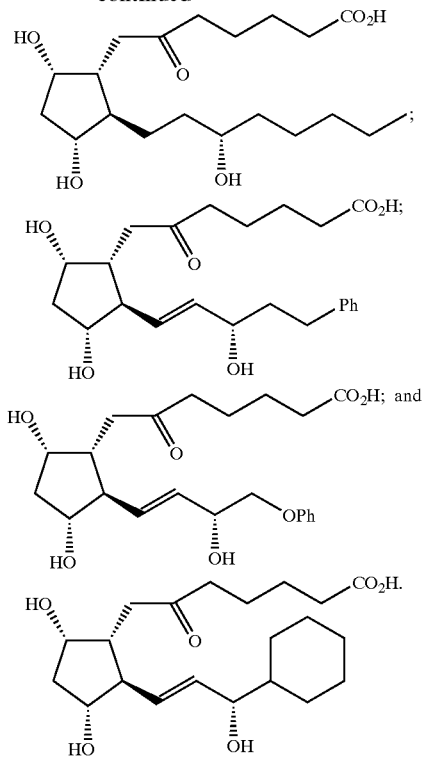

5. A compound of formula I:

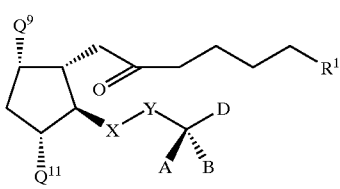

wherein:

$R^1$ is $(CH_2)_pCO_2R^2$, $(CH_2)_pOR^2$, $(CH_2)_pCOT$, or $(CH_2)_pT$, where:

R is H or pharmaceutically acceptable cationic salt moiety, or $CO_2R$ forms a pharmaceutically cceptable ester moiety;

$OR^2$ forms a free r functionally modified hydroxy group;

T comprises a free or functionally modified amino group; and p is 0 or 2;

$Q^9$ and $Q^{11}$ form a free or functionally modified hydroxy group;

X—Y is $CH_2CH_2$ or C≡C;

one of A, B is H and the other comprises a free or functionally modified hydroxy group, or A-B together are the oxygen of a carbonyl group; and D is cycloalkyl; or D is $(CH_2)_qAr$ or $(CH_2)_qOAr$; where q is 1–6; and Ar is a phenyl ring optionally substituted with alkyl, halo, trihalomethyl, alkoxy, acyl, acyloxy, amino, alkylamino, acylamino, or hydroxy; or D is $(CH_2)_pAr^1$; where p is 0–6; and

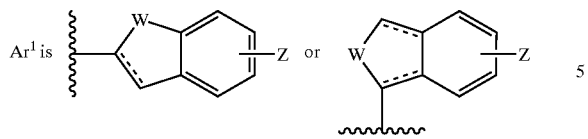

wherein:
W is $CH_2$, O, $S(O)_m$, $NR^{10}$, $CH_2CH_2$, CH=CH, $CH_2O$, $CH_2S(O)_m$, CH=N, or $CH_2NR^{10}$; where m is 0–2, and $R^{10}$ is H, alkyl, or acyl;

Z is H, alky, alkoxy, acyl, acyloxy, halo, trihalomethyl, amino, alkylamino, acylamino, or hydroxy; and ---- is single or double bond.

6. The compound of claim 5, wherein:

$R^1$ is $CO_2R$, wherein R is H, or $CO_2R$ forms an ophthalmically acceptable salt or an ophthalmically acceptable ester moiety;

$Q^9$ and $Q^{11}$ are OH;

X—Y is $CH_2CH_2$ or C≡C;

one of A, B=H, and the other is OH; and

D is $CH_2CH_2Ar$, $CH_2OAr$, pr cyclohexyl, where Ar is a phenyl ring optionally substituted with halo or trihalomethyl.

7. A compound selected from the group consisting of:

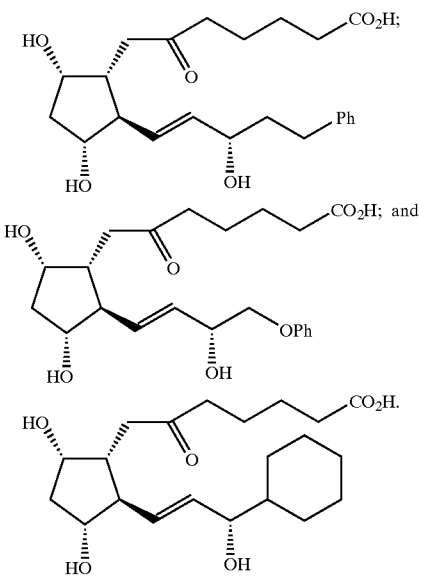

* * * * *

UNITED STATES PATENT AND TRADEMARK OFFICE
CERTIFICATE OF CORRECTION

PATENT NO.   : 6,576,663 B2
DATED        : June 10, 2003
INVENTOR(S)  : Peter G. Klimko Page 1 of 1

It is certified that error appears in the above-identified patent and that said Letters Patent is hereby corrected as shown below:

Column 10,
Lines 40-50, change " 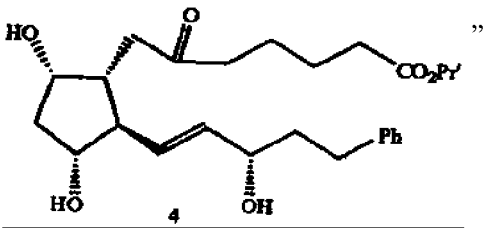 "

to -- 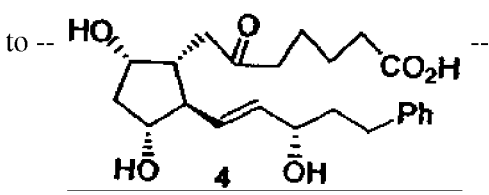 --

Signed and Sealed this

Twenty-second Day of March, 2005

JON W. DUDAS
*Director of the United States Patent and Trademark Office*